(12) United States Patent
Terada

(10) Patent No.: US 7,307,050 B2
(45) Date of Patent: Dec. 11, 2007

(54) AQUEOUS HAIR CLEANSING COMPOSITION COMPRISING A SULFATE SURFACTANT MIXTURE AND AN AMINO-MODIFIED SILICONE

(75) Inventor: Eiji Terada, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/313,740

(22) Filed: Dec. 22, 2005

(65) Prior Publication Data

US 2006/0154835 A1    Jul. 13, 2006

(30) Foreign Application Priority Data

Dec. 28, 2004  (JP) .............................. 2004-379726
Dec. 28, 2004  (JP) .............................. 2004-380127

(51) Int. Cl.
*C11D 1/37* (2006.01)
*C11D 9/36* (2006.01)

(52) U.S. Cl. ...................... 510/125; 510/119; 510/122; 510/127; 510/426; 510/428; 510/432; 510/466; 510/498; 510/536

(58) Field of Classification Search ................ 510/119, 510/122, 125, 127, 426, 428, 432, 466, 498, 510/536
See application file for complete search history.

(56) References Cited

U.S. PATENT DOCUMENTS

| | | | |
|---|---|---|---|
| 5,085,857 A | * | 2/1992 | Reid et al. ................ 424/70.12 |
| 6,171,515 B1 | | 1/2001 | Evans et al. |
| 6,277,360 B1 | * | 8/2001 | Carew et al. ............. 424/70.12 |
| 2002/0031483 A1 | * | 3/2002 | Beck et al. ................. 424/70.1 |
| 2006/0058205 A1 | * | 3/2006 | Ainger et al. ................ 510/119 |

FOREIGN PATENT DOCUMENTS

| | | |
|---|---|---|
| EP | 1 428 499 A2 | 6/2004 |
| EP | 1428499  * | 6/2004 |
| JP | 11-507079 | 6/1999 |
| WO | WO 97/35548 | 10/1997 |
| WO | WO 98/18443 | 5/1998 |
| WO | WO 03/066007 A1 | 8/2003 |

OTHER PUBLICATIONS

U.S. Appl. No. 11/313,850, filed Dec. 22, 2005, Terada.
U.S. Appl. No. 11/313,740, filed Dec. 22, 2005, Terada.

* cited by examiner

*Primary Examiner*—Charles Boyer
(74) *Attorney, Agent, or Firm*—Oblon, Spivak, McClelland, Maier & Neustadt, P.C.

(57) ABSTRACT

An aqueous hair cleansing composition made up of a sulfate surfactant, at least one amino-modified silicone and/or at least one water soluble cationic polymer, and a silicon oil.

9 Claims, No Drawings

AQUEOUS HAIR CLEANSING COMPOSITION COMPRISING A SULFATE SURFACTANT MIXTURE AND AN AMINO-MODIFIED SILICONE

FIELD OF THE INVENTION

The present invention relates to an aqueous hair cleansing composition containing a sulfate surfactant and an amino-modified silicone or cationic polymer.

BACKGROUND OF THE INVENTION

In recent years, there is a growing need for shampoos having conditioning effects such as smoothness of foam during foaming, smoothness of the hair during rinsing and a frictionless touch, as well as basic performances such as detergency, a good foaming property and an abundance of foam. A variety of amino-modified silicones are added to satisfy such a need. For example, a modified silicone having an average molecular weight from about 3000 to 100000 which is listed in the CTFA under the name of amodimethicone is incorporated in a shampoo. Shampoos containing such an amino-modified silicone are however unsatisfactory in its foaming property and its amount of foam volume and in addition, the smoothness provided by this silicone still remains unsatisfactory.

With a view to improving the smoothness property, a hair cosmetic composition containing an amino-modified silicone derivative in which a side chain bonded to a silicon atom has a group containing both a hydroxy group and a nitrogen atom is under investigation. For example, WO 2003/066007 pertains to a hair cosmetic composition containing an amino-modified silicone. Particularly in Example 1 of this document is described a shampoo composition using, as an anionic surfactant, sodium lauryl ether sulfate whose average number of moles of ethylene oxide addition is 2. The shampoo composition containing an amino-modified silicone derivative has however problems such as deterioration in the foaming property and a reduction in foam volume.

Alkyl sulfates typical as a component of a cleansing composition have been used most frequently because of their high detergency and power of producing an abundance of foam. When alkyl sulfates are used singly as an anionic component of a cleansing composition, however, hair feel imparted by shampooing is not satisfactory, because friction is caused between individual hairs. In order to improve the hair feel during shampooing, polyoxyethylene-added alkyl sulfates (alkyl ether sulfates), of which those having 2 to 3 moles, on average, of ethylene oxide have been employed because of good hair feel during shampooing. Although addition of ethylene oxide overcomes the problem of friction between individual hairs, it deteriorates the foaming speed greatly. Any one of the above-described methods is unsatisfactory for attaining quick foaming, good feel of the foam and the reduction in friction between hairs.

Alkyl ether sulfates added with 2 moles, on average, of ethylene oxide, which are typically and conventionally used an alkyl ether sulfates, are composed of about 20 wt. % of a 0 mole adduct, from 10 to less than 20 wt. % of 1, 2, and 3 mole adducts respectively, and the balance of 4 or greater mole adducts. The foaming property is therefore improved by adjusting the number of moles of ethylene oxide addition. For example, in JP-A-11-507079, described is an aqueous shampoo composition having a high conditioning effect, which contains from 5 to 50 wt. % of a surfactant component containing alkyl ether sulfates added with 1 to 8 moles of ethylene oxide and an amphoteric surfactant, and containing less than 5 wt. % of alkyl ether sulfates added with not greater than 1 mole of ethylene oxide. This shampoo composition is however unsatisfactory in both its foaming property and foam quality.

SUMMARY OF THE INVENTION

In the present invention, there is provided an aqueous hair cleansing composition containing the following components (A), (B) and (C):

(A) from 5 to 30 wt. % of a sulfate surfactant having sulfates which are represented by the following formula (1):

$$R-O-(C_2H_4O)_n-SO_3M \qquad (1)$$

(wherein, R represents a linear or branched $C_{8-18}$ alkyl or alkenyl group, n is 0 or a positive integer and M represents sodium or ammonium) and are composed of from 30 to 45 wt. % of a sulfate of the formula (1) in which n=0, from 18 to 27 wt. % of a sulfate of the formula (1) in which n=1, from 10 to 20 wt. % of a sulfate of the formula (1) in which n=2, and the balance of sulfates of the formula (1) in which n=3 or greater, and containing the sulfates of the formula (1) in which n=0 to 2 in a total amount of 70 wt. % or greater based on all the sulfates;

(B) one or more components selected from the following components (b1) and (b2):

(b1) from 0.05 to 10 wt. % of an amino-modified silicone derivative having, as a side chain bonded to a silicon atom, a group containing both a hydroxy group and a nitrogen atom, and (b2) from 0.01 to 3 wt. % of a water soluble cationic polymer having a molecular weight of from 100000 to 1900000 and a charge density from 0.6 to 4 meq/g, and (C) from 0.1 to 10 wt. % of a silicone oil represented by the following formula (2):

$$R'(CH_3)_2SiO-[(CH_3)_2SiO]_m-Si(CH_3)_2R' \qquad (2)$$

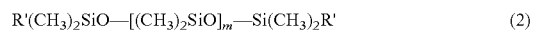

(wherein, R' represents a methyl or hydroxy group and m is a number of from 50 to 20000) and existing as disperse particles having an average particle size of less than 50 μm.

DETAILED DESCRIPTION OF THE INVENTION

The present invention relates to an aqueous hair cleansing composition which has a good foaming property and produces abundant foam during shampooing, has a very smooth foam quality, provides a smooth hair feel during rinsing, imparts hair with luster and manageability after drying, has good low-temperature stability and is substantially non-irritating.

The present inventors have found that a hair cleansing composition satisfying the above-described demands is obtainable by using polyoxyethylene added alkyl sulfates in which alkyl sulfates are distributed within a predetermined range on the smaller side of the number of moles of ethylene oxide addition, a specific amino-modified silicone derivative or a specific water soluble cationic polymer, and a silicone oil having a small particle size in combination.

The sulfate surfactant serving as Component (A) of the present invention is represented by the following formula (1):

$$R-O-(C_2H_4O)_n-SO_3M \qquad (1)$$

In the present invention, good foam quality, an abundant foam volume and fine hair feel can be attained by the sulfate surfactant having a specific distribution in the number of moles of ethylene oxide addition and having a high percentage of sulfates whose number of moles of EO addition is small, more specifically, the sulfate surfactant having a distribution which is composed of from 30 to 45 wt. % of a sulfate of the formula (1) in which n=0, from 18 to 27 wt. % of a sulfate of the formula (1) in which n=1, from 10 to 20 wt. % of a sulfate of the formula (1) in which n=2 and the balance of sulfates of the formula (1) in which n≧3 and containing the sulfates of the formula (1) in which n=0 to 2 in a total amount of 70 wt. % or greater based on all the sulfates. The sulfate surfactant having such a sulfate distribution is preferably composed of sulfates equal in alkyl chain length and only different in the number of moles of ethylene oxide addition.

In order to satisfy both the ability to quickly foam and a fine feel of foam, the sulfate surfactant having the following distribution in the number of moles of ethylene oxide addition, that is, the sulfate surfactant composed of from 33 to 43 wt. % of a sulfate with n=0, from 20 to 25 wt. % of a sulfate with n=1, from 13 to 18 wt. % of a sulfate with n=2 and the balance of sulfates with n>3 is preferred, in which that composed of from 35 to 41 wt. % of a sulfate with n=0, from 21 to 23 wt. % of a sulfate with n=1, from 14 to 17 wt. % of a sulfate with n=2 and the balance of sulfates with n>3 is more preferred. From the same viewpoint, the percentage of the sulfates with n=0 to 2 in the sulfate surfactant component is 70 wt. % or greater, with 70 to 85 wt. % based on all the sulfates is more preferred.

Such a sulfate surfactant can be prepared, for example, by sulfating an alcohol ethoxylate, which has been obtained by adding from 0.85 to 1.35 times the mole of ethylene oxide to a higher alcohol ROH, with from 0.95 to 1.0 equivalent of $SO_3$ and then neutralizing the resulting sulfate with sodium hydroxide or ammonia. In the formula (1), M is preferably ammonium from the viewpoint of the feel of foam.

The content of the sulfate surfactant as Component (A) in the aqueous hair cleansing composition of the present invention is from 5 to 30 wt. %. From the viewpoints of good foaming property, abundance of foam and foam quality with good smoothness during shampooing, it is preferably from 7 to 23 wt. %, more preferably from 10 to 20 wt. %.

Component (B) of the present invention is selected from (b1) an amino-modified silicone derivative and (b2) a water soluble cationic polymer.

The silicone derivative (b1) has, as a side chain bonded to a silicon atom, a group containing both a hydroxy group and a nitrogen atom. Preferred examples include those represented by the following average formula (3):

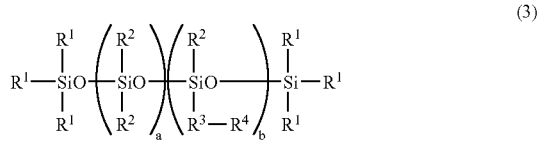

(wherein, $R^1$'s each independently represents a monovalent hydrocarbon group, hydroxy group or alkoxy group, $R^2$s each independently represents a monovalent hydrocarbon group, $R^3$ each independently represents a divalent $C_{1-10}$ hydrocarbon group, $R^4$ each independently represents a group represented by the following formula (4) or (5):

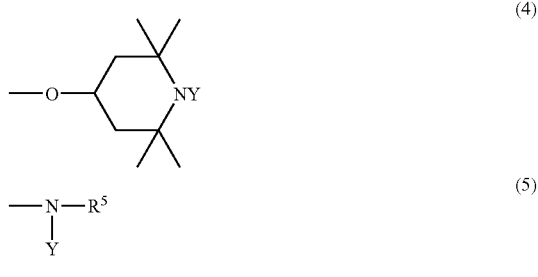

(in which, Y each independently represents a hydrogen atom or a group —$CH_2$—$CH(OH)$—$R^3$—OH, $R^5$ each independently represents a hydrogen atom or a group —$R^3NY_2$ (Y and $R^3$ have the same meanings as described above), with the proviso that all of the Y's do not represent a hydrogen atom simultaneously), "a" is a number from 25 to 1000 and "b" is a number from 1 to 200).

Examples of the monovalent hydrocarbon group as $R^1$ include alkyl and aryl groups. As $R^1$, $C_{1-3}$ alkyl groups (more preferably methyl group) and $C_{1-15}$ alkoxy groups, more preferably $C_{10-15}$ alkoxy groups are preferred.

Examples of the monovalent hydrocarbon group as $R^2$ include $C_{1-6}$ alkyl groups such as methyl, ethyl, propyl, butyl, pentyl and hexyl, $C_{6-10}$ aryl groups such as phenyl, tolyl and xylyl, and $C_{6-10}$ aralkyl groups such as benzyl and phenethyl. Of these, $C_{1-3}$ alkyl groups are preferred, with methyl group being more preferred.

Examples of the divalent $C_{1-10}$ hydrocarbon group as $R^3$ include alkylene groups such as methylene, ethylene, trimethylene, propylene, tetramethylene, methyltrimethylene, ethylethylene and dimethylethylene, and alkylene-arylene groups represented by —$(CH_2)_2$—$C_6H_4$—. Of these, $C_{2-4}$ alkylene groups are preferred.

As $R^4$, groups represented by the formula (4) are preferred, while as $R^5$, N-(2,3-dihydroxypropyl)aminoethyl and N,N-bis(2,3-dihydroxypropyl)aminoethyl are preferred. As the group —$CH_2$—$CH(OH)$—$R^3$—OH represented by Y, a 2,3-dihydroxypropyl group is preferred.

In the formula, "a" is preferably from 75 to 400, while "b" is preferably from 1 to 20.

The silicon derivative of (b1) can be synthesized, for example, by reacting, as described in EP0399706A2, an amino-modified silicone with an epoxy functional compound such as glycidol. The silicone derivative (b1) is, for example, any one of the compounds represented by the below-described formula and its commercially available product is, for example, "8500 Conditioning Agent" (CAS No. 237753-63-8) of Dow Corning.

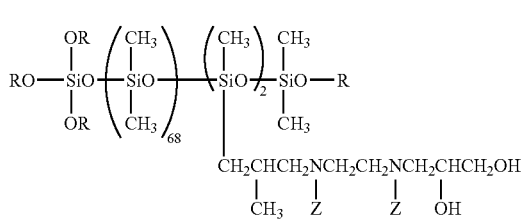

(wherein, R represents any one of hydrocarbon groups from $C_{13}H_{27}$ to $C_{15}H_{31}$, and 75% of Z represents a group —CH$_2$CH(OH)CH$_2$OH and the remaining portion represents a hydrogen atom).

As (b1), two or more of these compounds may be used in combination and the content thereof is from 0.05 to 10 wt. % in the cleansing composition of the present invention. From the viewpoints of the smoothness and softness of the hair from shampooing throughout rinsing, softness and smoothness after drying, it is preferably from 0.07 to 5 wt. %, more preferably from 0.1 to 3 wt. %.

The cationic polymer (b2) is a water soluble polymer having a molecular weight of from 100000 to 1900000 and a charge density of from 0.6 to 4 meq/g. From the viewpoints of smoothness during foaming and smoothness during rinsing, the molecular weight of (b2) is preferably from 200000 to 1800000, more preferably from 300000 to 1700000. The charge density is preferably from 0.6 to 3.8 meq/g, more preferably from 0.7 to 3.5 meq/g. The charge density of the water soluble cationic polymer may be measured by the colloid titration method using, for example, potassium polyvinylsulfate as a titration solution.

Specific examples of the water soluble cationic polymer include cationic cellulose derivatives, cationic starch, cationic guar gum derivatives, diallyl quaternary ammonium salt/acrylamide copolymer, quaternized polyvinylpyrrolidone derivatives, polyglycol polyamine condensates, vinyl imidazolium trichloride/vinylpyrrolidone copolymer, hydroxyethyl cellulose/dimethyldiallylammonium chloride copolymer, vinylpyrrolidone/quaternized dimethylaminoethyl methacrylate copolymers, polyvinylpyrrolidone/alkylaminoacrylate copolymers, polyvinylpyrrolidone/alkylaminoacrylate/vinylcaprolactam copolymers, vinylpyrrolidone/methacrylamidopropyl trimethylammonium chloride copolymer, alkylacrylamide/acrylate/alkylaminoalkylacrylamide/polyethyleneglycol methacrylate copolymers, adipic acid/dimethylaminohydroxypropyl ethylenetriamine copolymer ("Cartaretin", trade mark; product of Sandoz/USA), and cationic polymers as described in JP-A-1978-139734 and JP-A-1985-36407. Of these, cationic cellulose derivatives, cationic guar gum derivatives, and diallyl quaternary ammonium salt/acrylamide copolymers are preferred.

As (b1), commercially available products such as "Merquat 550" (trade name of acrylamide/diallyldimethylammonium salt copolymer, product of ONDEO-NALCO, CTFA name: Polyquaternium-7), "Luviquat FC370" (trade name of 1-vinyl-2-pyrrolidone/1-vinyl-3-methylimidazolium copolymer, product of BASF, CTFA name: Polyquaternium-16), "Gafquat 755N" (trade name of 1-vinyl-2-pyrrolidone/dimethylaminoethyl methacrylate copolymer, product of ISP, CTFA name: Polyquaternium-11), "Ucare polymer JR and LR series" (trade names of a salt as a reaction product between trimethylammonium substituted epoxide and hydroxyethyl cellulose, product of Amerchol, CTFA name: Polyquaternium-10), "Poiz C-60H", "Poiz C-80M", and "Poiz C-150L" (each, trade name of a salt as a reaction product between trimethylammonium substituted epoxide and hydroxyethyl cellulose: product of Kao Corp. CTFA name: Polyquaternium-10), and "Jaguar series" (trade name of guar hydroxypropyltrimonium chloride, product of Rhodia).

The above-described cationic polymers (b2) may be used either singly or in combination. The content thereof is from 0.01 to 3 wt. % in the cleansing composition of the present invention. From the viewpoints of smoothness from shampooing through rinsing, the content is preferably from 0.05 to 2 wt. %, more preferably from 0.1 to 1 wt. %.

The silicone oil serving as Component (C) of the present invention is represented by the formula (2) and exists as disperse particles having an average particle size of less than 50 μm. It is substantially water insoluble and nonvolatile. Component (C) is preferably a water-insoluble highly-polymerized dimethylpolysiloxane emulsion obtained by emulsion polymerization.

The average particle size of the disperse particles of the silicone oil as Component (C) is less than 50 μm, preferably not greater than 4 μm, more preferably not greater than 3 μm, even more preferably not greater than 2 μm. From the viewpoints of feeling upon use and conditioning effects, however, the average particle size is preferably 0.1 μm or greater.

As such a silicone oil, a silicon emulsion commercially available as "Silicone CF2450" from Dow Corning Toray which contains 60 wt. % of a dimethylpolysiloxane oil of the formula (2) in which m is from 300 to 6500, and has an average particle size of 0.5 μm can be used, for example.

The silicone oil having such a small particle size as Component (C) is incorporated in an amount of from 0.01 to 10 wt. %, preferably from 0.05 to 6 wt. %, more preferably from 0.5 to 3 wt. %, an even more preferably from 1 to 2 wt. % in the aqueous hair cleansing composition of the present invention in order to improve the feel of foam during shampooing, and hair feel and luster after drying.

To the aqueous hair cleansing composition of the present invention, a nonionic surfactant or amphoteric surfactant may be added in order to improve its detergency.

Examples of the nonionic surfactant include polyoxyalkylene sorbitan fatty acid esters, polyoxyalkylene sorbitol fatty acid esters, polyoxyalkylene glycerol fatty acid esters, polyoxyalkylene fatty acid esters, polyoxyalkylene alkyl ethers, polyoxyalkylene alkyl phenyl ethers, polyoxyalkylene (hydrogenated) castor oils, sucrose fatty acid esters, polyglyceryl alkyl ethers, polyglyceryl fatty acid esters, fatty acid alkanolamides, alkyl glycosides, monoalkyl glyceryl ethers, and monoalkenyl glyceryl ethers. Of these, alkyl glycosides, polyoxyalkylene (C$_8$-C$_{20}$) fatty acid esters, polyoxyethylene sorbitan fatty acid esters, polyoxyethylene hydrogenated castor oil, fatty acid alkanolamides, monoalkylglyceryl ether and monoalkenylglyceryl ether are preferred.

The fatty acid alkanolamides may be either monoalkanolamides or dialkanolamides. Those having a C$_{8-18}$ acyl group are preferred, with those having a C$_{10-16}$ acyl group being more preferred. Those having a C$_{2-3}$ hydroxyalkyl group are even more preferred. Examples include oleic diethanolamide, palm kernel oil fatty acid diethanolamide, coconut oil fatty acid diethanolamide, lauric diethanolamide, polyoxyethylene coconut oil fatty acid monoethanolamide, coconut oil fatty acid monoethanolamide, lauric isopropanolamide, and lauric monoethanolamide.

Of the monoalkyl glyceryl ethers and monoalkenyl glyceryl ethers, the former ones are preferred. As the alkyl group of them, C$_{4-10}$ alkyl groups are preferred, with linear or branched C$_{8-10}$ alkyl groups being more preferred. Specific examples include n-butyl, isobutyl, n-pentyl, 2-methylbutyl, isopentyl, n-hexyl, isohexyl, n-heptyl, n-octyl, 2-ethylhexyl, n-decyl and isodecyl groups. Of these, 2-ethylhexyl and isodecyl groups are preferred.

Examples of the amphoteric surfactant include betaine surfactants. Of these, betaine surfactants such as alkyldimethylaminoacetic acid betaines, fatty acid amidopropylbetaines and alkylhydroxysulfobetaines are preferred, of which fatty acid amidopropylbetaines are more preferred. The fatty acid amidopropylbetaines preferably have a $C_{8-18}$ acyl group, more preferably a $C_{10-16}$ acyl group. Preferred specific examples include lauric acid amidopropylbetaine, palm kernel oil fatty acid amidopropylbetaine and coconut oil fatty acid amidopropylbetaine.

For the aqueous hair cleansing composition of the present invention, these nonionic or amphoteric surfactants may be used either singly or in combination. In order to formulate the aqueous hair cleansing composition of the present invention into an aqueous liquid cleansing composition, however, use of the fatty acid amidopropylbetaine or fatty acid alkanolamide as a surfactant other than Component (A) in combination with Component (A) is desired because this makes it possible not only to further improve the foaming power but also to give the composition with adequate liquid properties.

The content of the nonionic or amphoteric surfactant is preferably from 0.1 to 15 wt. % in the hair cleansing composition of the present invention, but is more preferably from 0.1 to 10 wt. %, even more preferably from 0.5 to 8 wt. %, even more preferably from 1 to 6 wt. % in order to increase the foam volume.

In the present invention, one or more anionic surfactants other than the sulfate surfactant may be added. Examples of them include sulfonate surfactants and carboxylate surfactants such as alkyl sulfosuccinates, polyoxyalkylene alkyl sulfosuccinates, higher fatty acid salts, alkanesulfonates, and alkyl ether carboxylic acids or salts thereof.

Furthermore, the aqueous hair cleansing composition of the present invention may contain a cationic surfactant and a conditioning component such as a silicone other than the components (b1) and (C) in order to improve the finish of the Hair after drying.

Examples of the cationic surfactant include alkyltrimethylammonium salts, alkoxytrimethylammonium salts, dialkyldimethylammonium salts, alkyldimethylamines and salts thereof, alkoxydimethylamines and salts thereof, and alkylamidodimethylamines and salts thereof.

(i) Alkyltrimethylammonium Salts

They are, for example, represented by the following formula:

$$R^{11}-N^+(Me)_3X^-$$

(wherein, $R^{11}$ represents a $C_{12-22}$ alkyl group, Me represents a methyl group, and $X^-$ represents a halogen (chlorine or bromine) ion or a $C_{1-2}$ alkylsulfate ion).

(ii) Alkoxytrimethylammonium Salts

They are, for example, represented by the following formula:

$$R^{12}-O-R^{13}-N^+(Me)_3X^-$$

(wherein, $R^{12}$ represents a $C_{12-22}$ alkyl group, $R^{13}$ represents an ethylene or propylene group, Me represents a methyl group, and $X^-$ has the same meaning as described above).

(iii) Dialkyldimethylammonium Salts

They are, for example, represented by the following formula:

$$R^{14}{}_2-N^+(Me)_2X^-$$

(wherein, $R^{14}$ represents a $C_{12-22}$ alkyl group or a benzyl group, Me represents a methyl group, and $X^-$ has the same meaning as described above).

(iv) Alkyldimethylamines and Salts Thereof

They are, for example, represented by the following formula:

$$R^{15}-N(Me)_2$$

(wherein, $R^{15}$ represents a $C_{12-22}$ alkyl group, and Me represents a methyl group).

(v) Alkoxydimethylamines and Salts Thereof

They are, for example, represented by the following formula:

$$R^{16}-O-R^{17}-N(Me)_2$$

(wherein, $R^{16}$ represents a $C_{12-22}$ alkyl group, $R^{17}$ represents an ethylene or propylene group and Me represents a methyl group).

(vi) Alkylamidodimethylamines and Salts Thereof

They are, for example, represented by the following formula:

$$R^{18}-C(=O)NH-R^{19}-N(Me)_2$$

(wherein, $R^{18}$ represents a $C_{11-21}$ alkyl group, $R^{19}$ represents an ethylene or propylene group and Me represents a methyl group).

Examples of the cationic surfactant other than those described in (i) to (vi) include lanolin fatty acid aminopropylethyldimethylammonium ethyl sulfate (ethyl sulfate salt of alkanoylaminopropyldimethylethylammonium, said alkanoyl group being derived from lanolin), lanolin fatty acid aminoethyltriethylammonium ethyl sulfate, lanolin fatty acid aminopropyltriethylammonium ethyl sulfate, lanolin fatty acid aminoethyltrimethylammonium methyl sulfate, lanolin fatty acid aminopropylethyldimethylammonium methyl sulfate, isoalkanoic acid ($C_{14}$-$C_{20}$) aminopropylethyldimethylammonium ethyl sulfate, isoalkanoic acid ($C_{18}$-$C_{22}$) aminopropylethyldimethylammonium ethyl sulfate, isostearic acid aminopropylethyldimethylammonium ethyl sulfate, isononanoic acid aminopropylethyldimethylammonium ethyl sulfate, and alkyltrimethylammonium saccharins.

These cationic surfactants may be used in combination of two or more. The content thereof is preferably from 0.01 to 10 wt. %, more preferably from 0.05 to 6 wt. %, even more preferably from 0.3 to 3 wt. %, even more preferably from 0.5 to 2 wt. % in the aqueous hair cleansing composition of the present invention from the viewpoint of smoothness of the hair from shampooing through rinsing.

As the silicone other than Components (b1) and (C), those listed below can be used, for example.

(1) Dimethylpolysiloxane

As the dimethylpolysiloxane other than Component (C), either a volatile dimethylpolysiloxane or low-molecular-weight liquid nonvolatile dimethylpolysiloxane may be used in combination. Commercially available products include "SH200" (trade name; product of Dow Corning Toray) and "KF96" (trade name; product of Shin-etsu Chemical).

(2) Amino-Modified Silicones

Various amino-modified silicones other than Component (b1) of the present invention may be used. Those having an average molecular weight from about 3000 to 100000 which is listed under the name of "Amodimethicone" in the third edition of the CTFA Dictionary (Cosmetic Ingredient Dictionary/USA) are preferred. These amino-modified silicones are preferably employed as an aqueous emulsion. Commercially available products include "SM 8704C" (trade name;

product of Dow Corning Toray), "DC 929" (trade name; product of Dow Corning) and "KT1989" (product of GE Toshiba Silicones).

(3) Other Silicones

Examples of the silicone other than those described above include polyether modified silicones, methylphenylpolysiloxane, fatty acid modified silicones, alcohol modified silicones, alkoxy modified silicones, epoxy modified silicones, fluorine modified silicones, cyclic silicones and alkyl modified silicones.

Two or more of these silicones other than Components (B) and (C) may be used in combination. The content thereof in the aqueous hair cleansing composition of the present invention is preferably from 0.01 to 10 wt. %, more preferably from 0.05 to 6 wt. %, even more preferably from 0.3 to 3 wt. %, even more preferably from 0.5 to 2 wt. % from the viewpoint of the smoothness of the hair from shampooing through rinsing.

The aqueous hair cleansing composition of the present invention may contain an oil agent as another conditioning agent. Examples of the oil agent include hydrocarbons such as squalene, squalane, liquid paraffin, liquid isoparaffin, and cycloparaffin; glycerides such as castor oil, cacao oil, mink oil, avocado oil, and olive oil; waxes such as beeswax, whale wax, lanolin, and carnauba wax; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate and tridecyl isononanoate; higher fatty acids such as capric acid, lauric acid, myristic acid, palmitic acid, stearic acid, behenic acid, oleic acid, coconut oil fatty acids, isostearic acid, and isopalmitic acid; higher alcohols such as myristyl alcohol, cetyl alcohol, oleyl alcohol, stearyl alcohol, isostearyl alcohol, behenyl alcohol, 2-octyldodecanol and cetostearyl alcohol; isostearyl glyceryl ether; and polyoxypropylene butyl ether. Of these, higher alcohols, for example, myristyl alcohol, cetyl alcohol and stearyl alcohol are preferred. These oil agents may be use either singly or in combination of two or more. The content thereof is preferably from 0.2 to 2 wt. %, more preferably from 0.3 to 1.8 wt. %, and even more preferably from 0.5 to 1.5 wt. % in the aqueous hair cleansing composition of the present invention.

In addition, a pearling agent containing an ethylene glycol monoalkyl ester or ethylene glycol dialkyl ester may be incorporated in the cleansing composition to improve its texture and stability. Examples of the ethylene glycol monoalkyl ester include ethylene glycol monostearyl ester and ethylene glycol monobehenyl ester, while those of the ethylene glycol dialkyl ester include ethylene glycol distearyl ester and ethylene glycol dibehenyl ester. Two or more of them may be used in combination. The content of the pearling agent in the aqueous hair cleansing composition of the present invention is preferably from 0.5 to 8 wt. %, more preferably from 0.7 to 5 wt. %, and even more preferably from 1 to 3 wt. %. In view of improving the stability of the cleansing composition, the weight ratio of the pearling agent to the sulfate surfactant (pearling agent/sulfate surfactant) in the hair cleansing composition of the present invention is preferably from 1/10 to 2/5, more preferably from 1/7 to 3/10, and even more preferably from 1/6 to 1/4.

The aqueous hair cleansing composition of the present invention may contain a viscosity regulator. Examples of the viscosity regulator include hydroxyethyl cellulose, methyl cellulose, polyethylene glycol, polypropylene glycol, ethylene glycol, propylene glycol, isoprene glycol, ethanol, benzyl alcohol, benzyl oxyethanol, phenoxyethanol, clay minerals, and salts (sodium chloride, ammonium chloride, sodium citrate and the like). Of these, salts are preferred, with sodium chloride and sodium citrate being more preferred. Two or more of the viscosity regulators may be used in combination. The content thereof in the aqueous hair cleansing composition of the present invention is preferably from 0.01 to 5 wt. %, more preferably from 0.05 to 3 wt. %, and even more preferably from 0.1 to 1.5 wt. % from the standpoints of the volume and quality of foam.

In addition to the above-described components, components which are employed in ordinary hair cleansing compositions can also be incorporated in the aqueous hair cleansing composition of the present invention as needed depending upon the purpose of use. Such components include, for example, antidandruff agents; vitamin preparations; bactericides; anti-inflammatories; antiseptics; chelating agents; humectants such as sorbitol, panthenol and glycerin; colorants such as dyes and pigments; extracts such as extracts of eucalyptus in a polar solvent, proteins available from shells having a pearl layer or pearls or hydrolysates thereof, proteins available from silk or hydrolysates thereof, protein-containing extracts available from seeds of legume, Asian ginseng extract, rice bran extract, fucus vesiculosus extract, aloe extract, Alpinia Leaf extract, and chlorella extract; pearling agents such as titanium oxide; perfumes; coloring matters; ultraviolet absorbers; antioxidants; and other components described in ENCYCLOPEDIA OF SHAMPOO INGREDIENTS (MICELLE PRESS).

The aqueous hair cleansing composition of the present invention has preferably a pH (diluted with 20 times the amount of water, 25° C.) from 2 to 6, more preferably from 3 to 5, even more preferably from 3.5 to 4.5 when it is applied to the hair, from the viewpoint of improving the luster and manageability of the hair. As a pH regulator, an organic acid is preferred, with an α-hydroxy acid being more preferred. Specific preferred examples of it include malic acid, citric acid, lactic acid and glycolic acid. As the pH regulator, two or more of these organic acids may be used in combination. The amount of use thereof is preferably from 0.01 to 5 wt. %, more preferably from 0.1 to 3 wt. %, and even more preferably from 0.3 to 2 wt. % in the aqueous hair cleansing composition of the present invention from the viewpoints of improvement in foam quality and flexibility of hair during shampooing. As another pH regulator, a base such as sodium hydroxide, potassium hydroxide or ammonium chloride may be used in combination with the above-described organic acid.

Although the form of the aqueous hair cleansing composition of the present invention can be chosen as desired from a liquid form, a gel form and the like, a liquid form in a solvent such as water or a lower alcohol is preferred, with the former one being more preferred.

The following examples further describe and demonstrate embodiments of the present invention. The examples are given only solely for the purpose of illustration and are not to be construed as limitations of the present invention.

EXAMPLES

Preparation Example 1

Preparation of ammonium lauryl ether sulfate Added with 1.0 Mole, on Average, of EO In a pressure-tight hermetically-sealed reactor were charged with 2000 g of "Kalcol 2470" (trade name; product of Kao, dodecyl alcohol:tetradecyl alcohol=about 3:1) and 1.45 g of potassium hydroxide. After dehydration at 110° C. and 10 mmHg for 30 minutes, the temperature in the system was raised to 165° C. Then, 456 g of ethylene oxide was pressed into the reactor and the addition reaction was conducted for 30 minutes without changing the temperature. The reaction mixture was then cooled to 80° C., and neutralized with 1.3 g of acetic acid, whereby an ethylene oxide adduct of the above-described raw material alcohol was obtained.

A sulfation reaction was then effected at 40° C. by using 1793 g of the mixture obtained by the above-described operation and 607 g of a sulfuric acid gas. After completion of the reaction, the reaction mixture was neutralized with 150 g of 28 wt. % aqueous ammonia and 600 g of deionized water. The concentration and pH of the neutralized mixture were adjusted further with 28 wt. % aqueous ammonia and deionized water, whereby 10000 g of Sulfate 1 (a 25 wt. % aqueous solution) as shown in Table 1 was obtained.

The sulfate, anion and EO chain of the resulting Sulfate 1 were confirmed in accordance with the Japanese Standards of Cosmetic Ingredients, while a component ratio was analyzed by gas chromatography. They are shown in Table 1.

Preparation Example 2

Preparation of ammonium lauryl ether sulfate Added with 1.3 Moles, on Average, of EO In a similar manner to that employed in Preparation Example 1 except for a change in the reaction ratio of the raw materials, Sulfate 2 (a 25 wt. % aqueous solution) as shown in Table 1 was obtained.

The sulfate, anion and EO chain of the resulting Sulfate 2 were confirmed in accordance with the Japanese Standards of Cosmetic Ingredients, while a component ratio was analyzed by gas chromatography. They are shown in Table 1.

Preparation Example 3

Preparation of sodium lauryl ether sulfate Added with 1.0 Mole, on Average, of EO A sulfation reaction was effected at 40° C. by using 1793 g of the ethylene oxide adduct of the raw material alcohol obtained in Preparation Example 1 and 607 g of a sulfuric acid gas. After completion of the reaction, the reaction mixture was neutralized with 132 g of a 23 wt. % aqueous solution of sodium hydroxide and 556 g of deionized water. The concentration and pH of the neutralized mixture were adjusted with a 23 wt. % aqueous solution of sodium hydroxide, 75 wt. % of phosphoric acid and deionized water, whereby 10000 g of Sulfate 3 (a 25 wt. % aqueous solution) as shown in Table 1 was obtained.

The sodium salt, sulfate, anion and EO chain of the resulting Sulfate 3 were confirmed in accordance with the Japanese Standards of Cosmetic Ingredients, while a component ratio was analyzed by gas chromatography. They are shown in Table 1.

TABLE 1

| | $n=0$ | $n=1$ | $n=2$ | $n=3$ | (wt. %) $n \geq 4$ |
|---|---|---|---|---|---|
| Sulfate 1 of Preparation Example 1 Ammonium lauryl ether sulfate added with 1.0 mole, on average, of EO | 40.64 | 22.29 | 14.80 | 8.68 | 13.59 |
| Sulfate 2 of Preparation Example 2 Ammonium lauryl ether sulfate added with 1.3 moles, on average, of EO | 34.29 | 21.41 | 16.59 | 10.09 | 17.62 |
| Sulfate 3 of Preparation Example 3 Sodium lauryl ether sulfate added with 1.0 mole, on average, of EO | 40.64 | 22.29 | 14.80 | 8.68 | 13.59 |
| Comparative Sulfate 1 *[1] Sodium lauryl ether sulfate added with 2.0 moles, on average, of EO | 19.97 | 15.99 | 16.03 | 13.20 | 34.82 |
| Comparative Sulfate 2 *[2] Mixture of sodium lauryl ether sulfate added with 2.0 moles, on average, of EO ("Emal 227-PH11") and sodium lauryl sulfate | 46.43 | 10.70 | 10.73 | 8.83 | 23.31 |

*[1] Comparative Sulfate 1 "Emal 227-PH11" of Kao which is a 27 wt. % aqueous solution of sulfate (sodium lauryl ether sulfate added with 2.0 moles, on average, of EO)
*[2] Comparative Sulfate 2 Mixture of sodium lauryl ether sulfate added with 2.0 moles, on average, of EO and sodium lauryl sulfate. A 27 wt. % aqueous solution of the sulfate was obtained by mixing 1000 g of "Emal 227-PH11" and 500 g of "Emal 2F-HP", each product of Kao.

Examples 1 to 6, and Comparative Examples 1 to 3

Hair cleansing compositions as shown in Table 2 were prepared using sulfate surfactants as shown in Table 1 and foaming speed, smoothness of the hair when shampooed with them, and luster and manageability of the hair after drying were evaluated. The pH is a value as measured at 25° C. after dilution with 20 times the amount of water.

(Foaming Speed)

By employing the apparatus and conditions as described in [0053] and [0054] of JP-A-1998-73584, the foam volume thus produced was measured using 1.5 mL of a sample to be evaluated and 0.3 mL of a model sebum and the foaming speed was evaluated based on the time until the foam volume reached 25 mL.

Criteria for Evaluation:
  A: less than 100 seconds
  B: 100 seconds or greater but less than 200 seconds
  C: 200 seconds or greater but less than 300 seconds
  D: 300 seconds or greater (Smoothness of the Hair During Shampooing Through Rinsing)

After a human hair bundle of 25 cm in length, 5.5 cm in width and 10 g in weight was rinsed lightly with warm water of 40° C., and excess water was removed. The hair cleansing composition (0.5 g) was foamed sufficiently for about 30 seconds to shampoo the hair bundle and the smoothness of the foamed hair bundle was organoleptically evaluated. Then, the smoothness was organoleptically evaluated while rinsing the hair bundle with warm water of 40° C. Evaluation was carried out by a panel of five experts and their total scores were indicated.

Criteria for Evaluation:
  4: Very smooth
  3: Smooth

2: not so smooth
1: Not smooth (Luster and Manageability After Drying)

A hair bundle treated in a similar manner to that employed in the evaluation of smoothness was rinsed for 30 seconds with running water (2 L/min) of 40° C. and then towel-dried sufficiently. After natural drying, the luster and manageability were evaluated visually. They were evaluated by a panel of 5 experts and their total scores were indicated.

Criteria for Evaluation:
4: Very good
3: Good
2: Not so good
1: Not good

TABLE 2

| | (wt. %) | Example 1 | Example 2 | Example 3 | Example 4 | Example 5 | Example 6 | Comp. Ex. 1 | Comp. Ex. 2 | Comp. Ex. 3 |
|---|---|---|---|---|---|---|---|---|---|---|
| (A) | Sulfate 1 of Preparation Example 1 (Ammonium salt added with 1.0 mole, on average, of EO, a 25 wt. % aqueous solution) | 48 | 48 | 34 | 64 | | | 48 | | |
| | Sulfate 2 of Preparation Example 2 (Ammonium salt added with 1.3 moles, on average, of EO, a 25 wt. % aqueous solution) | | | | | 48 | | | | |
| | Sulfate 3 of Preparation Example 3 (Sodium salt added with 1.0 mole, on average, of EO, a 25 wt. % aqueous solution) | | | | | | 48 | | | |
| (A') | Comparative Sulfate 1 (Sodium salt added with 2.0 moles, on average, of EO, a 27 wt. % aqueous solution) | | | | | | | | 44.4 | |
| | Comparative Sulfate 2 (Mixture of sodium salts, a 27 wt. % aqueous solution) | | | | | | | | | 44.4 |
| (b1) | Amino-modified silicone ("8500 Conditioning Agent", product of Dow Corning) *3 | 0.5 | 0.5 | 1.0 | 0.3 | 0.5 | 0.5 | | 0.5 | |
| (b1') | Amino-modified silicone ("KT1989", product of GE Toshiba Silicones) *4 | | | | | | | 0.5 | | 0.5 |
| (C) | Highly-polymerized methylpolysiloxane emulsion ("Silicone CF2450", product of Dow Corning Toray) *5 | | | | | 2 | | | | |
| Others | Lauryl amidopropylbetaine | | | | | 2 | | | | |
| | Myristyl alcohol | | | | | 1 | | | | |
| | Cocoyl monoethanolamide | | | | | 0.5 | | | | |
| | Ethylene glycol distearate | | | | | 2 | | | | |
| | Cationic hydroxyethyl cellulose ("Poiz C-80M", product of Kao corporation) *6 | | | | | 0.5 | | | | |
| | Benzyl alcohol | | | | | 0.5 | | | | |
| | Malic acid | 0.75 | 0.03 | 0.75 | 0.75 | 0.75 | 0.75 | 0.75 | 0.75 | 0.75 |
| | Sodium chloride | | | | | 0.2 | | | | |
| | Purified water | | | | | Balance | | | | |
| | Total | | | | | 100 | | | | |
| | pH | 3.7 | 5.5 | 3.5 | 3.9 | 3.7 | 3.7 | 3.7 | 3.7 | 3.7 |
| Evaluation | Foaming speed | A | A | A | A | A | A | A | C | B |
| | Smoothness of foam | 20 | 20 | 17 | 20 | 17 | 18 | 14 | 10 | 12 |
| | Smoothness of the hair during rinsing | 20 | 20 | 20 | 19 | 19 | 18 | 14 | 12 | 10 |
| | Luster and manageability | 20 | 15 | 20 | 19 | 19 | 20 | 18 | 18 | 18 |

*3 "DC8500" (trade name; product of Dow Corning)

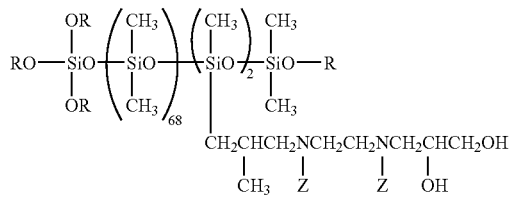

R: a hydrocarbon group selected from $C_{13}H_{27}$ to $C_{15}H_{31}$
Z: 75% represents a group —$CH_2CH(OH)CH_2OH$ and 25% represents a hydrogen atom
*4 "KT1989" (trade name; product of GE Toshiba)

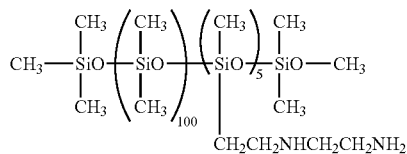

*5 represented by the formula (2) wherein m is from 300 to 6500, having an average particle size of 0.5 µm and having a content of 60 wt. %.
*6 molecular weight: 800000, Cationic charge density: 1.1 meq/g Examples 7 to 13 and Comparative Examples 4 to 6

Hair cleansing compositions as shown in Table 3 were prepared using the sulfate surfactants as shown in Table 1. In a similar manner to that described above, foaming speed, smoothness during shampooing, and luster and manageability of the hair after drying were evaluated. The pH is a value as measured at 25° C. when the composition is diluted with 20 times the amount of water.

-continued

| | (wt. %) |
|---|---|
| Cationic hydroxyethyl cellulose *[11] | 0.4 |
| Amino-modified silicone derivative *[3] | 1.0 |
| Highly polymerized methylpolysiloxane emulsion ("Silicone CF2450", trade name; product of Dow Corning Toray) | 1.5 |

TABLE 3

| | (Wt. %) | Example | | | | | | | Comp. Ex. | | |
|---|---|---|---|---|---|---|---|---|---|---|---|
| | | 7 | 8 | 9 | 10 | 11 | 12 | 13 | 4 | 5 | 6 |
| (A) | Sulfate 1 of Preparation Example 1 (Ammonium salt added with 1.0 mole, on average, of EO, a 25 wt. % aqueous solution) | 48 | 48 | 48 | 34 | 64 | | | 48 | | |
| | Sulfate 2 of Preparation Example 2 (Ammonium salt added with 1.3 moles, on average, of EO, a 25 wt. % aqueous solution) | | | | | | 46 | | | | |
| | Sulfate 3 of Preparation Example 3 (Sodium salt added with 1.0 mole, on average, of EO, a 25 wt. % aqueous solution) | | | | | | | 46 | | | |
| (A') | Comparative Sulfate 1 (Sodium salt added with 2.0 moles, on average, of EO, a 27 wt. % aqueous solution) | | | | | | | | | 48 | |
| | Comparative Sulfate 2 (Mixture of sodium salts, a 27 wt. % aqueous solution) | | | | | | | | | | 48 |
| (b2) | Cationic hydroxyethyl cellulose ("Polymer JR-30M", product of Amerchol) *[7] | 0.5 | 0.5 | | 0.7 | 0.3 | 0.5 | 0.5 | | | |
| | Diallyl quaternary ammonium salt/acrylamide copolymer ("Mequat 550", product of ONDEO-NALCO) *[8] | | | 0.5 | | | | | | 0.5 | |
| (b2') | Cationic hydroxyethyl cellulose ("Catinal HC200", product of Toho Chemical Industry) *[9] | | | | | | | | 0.5 | | |
| | Dimethyldiallylammonium chloride homopolymer ("Merquat 100", product of ONDEO-NALCO) *[10] | | | | | | | | | | 0.5 |
| (C) | Highly polymerized methylpolysiloxane emulsion ("CF2450", product of Dow Corning Toray) *[5] | | | | | | 1 | | | | |
| Others | Lauryl amidopropylbetaine | | | | | | 2 | | | | |
| | Myristyl alcohol | | | | | | 1 | | | | |
| | Cocoyl monoethanolamide | | | | | | 0.5 | | | | |
| | Ethylene glycol distearate | | | | | | 2 | | | | |
| | Benzyl alcohol | | | | | | 0.5 | | | | |
| | Malic acid | 0.75 | 0.03 | 0.75 | 0.75 | 0.75 | 0.75 | 0.75 | 0.75 | 0.75 | 0.75 |
| | Sodium chloride | | | | | | 0.2 | | | | |
| | Purified water | | | | | | Balance | | | | |
| | Total | | | | | | 100 | | | | |
| | pH | 3.7 | 5.5 | 3.7 | 3.5 | 3.9 | 3.7 | 3.7 | 3.7 | 3.7 | 3.7 |
| Evaluation | Foaming speed | A | A | A | A | A | A | A | A | C | B |
| | Smoothness of foam | 20 | 20 | 18 | 17 | 20 | 17 | 18 | 14 | 6 | 13 |
| | Smoothness of hair during rinsing | 20 | 20 | 18 | 20 | 18 | 19 | 18 | 14 | 10 | 14 |
| | Luster, manageability | 20 | 15 | 19 | 20 | 18 | 19 | 20 | 18 | 18 | 18 |

*[7] molecular weight: 900000, Cationic charge density: 1.2 meq/g
*[8] molecular weight: 1500000, Cationic charge density: 3.1 meq/g
*[9] molecular weight: 2000000, Cationic charge density: 0.8 meq/g
*[10] molecular weight: 50000, Cationic charge density: 6.2 meq/g Example 14

Pearlescent Shampoo

| | (wt. %) |
|---|---|
| Sulfate 3 (sodium salt, a 25 wt. % aqueous solution) obtained in Preparation Example 3 | 48.0 |
| Sodium cocoamphoacetate | 0.5 |
| Cocoyl monoethanolamide | 0.3 |
| Polyoxyethylene (14) lauryl ether | 1.0 |
| Ethylene glycol distearate | 2.0 |

-continued

| | (wt. %) |
|---|---|
| Panthenol | 0.05 |
| Silk extract | 0.05 |
| Sodium chloride | 1.0 |
| Lactic acid | Amount to adjust pH to 6.0 |
| Deionized water | Balance |

*[11] "Polymer JR-400", trade name; product of Amerchol (molecular weight: 400000, cationic charge density: 1.2 meq/g)

Example 15

Conditioning Shampoo

| | (wt. %) |
|---|---|
| Sulfate salt 1 (ammonium salt, a 25 wt. % aqueous solution) obtained in Preparation Example 1 | 52.0 |
| Isodecyl glyceryl ether | 0.7 |
| Lauryl amidopropylbetaine | 2.0 |
| Cocoyl monoethanolamide | 0.5 |
| Myristyl alcohol | 1.5 |
| Polyoxyethylene (16) lauryl ether | 1.0 |
| Ethylene glycol distearate | 2.0 |
| Cationic hydroxyethyl cellulose *6 | 0.5 |
| Diallyl quaternary ammonium salt/acrylamide copolymer *8 | 0.2 |
| Amino-modified silicone derivative *3 | 0.4 |
| Highly polymerized methylpolysiloxane emulsion ("Silicone CF2450", trade name; product of Dow Corning Toray) | 4.0 |
| Benzyl alcohol | 0.4 |
| Polypropylene glycol (Mw = 400) | 0.2 |
| Sodium chloride | 1.0 |
| Hydrolyzed conchiolin solution (dry content: 3 wt. %) | 0.05 |
| Asian ginseng extract (dry content: 3 wt. %) | 0.05 |
| Soybean extract (dry content: 0.4 wt. %) | 0.05 |
| Eucalyptus extract (dry content: 0.2 wt. %) | 0.05 |
| Rice bran oil | 0.05 |
| Malic acid | 0.5 |
| Sodium hydroxide | Amount to adjust pH to 3.9 |
| Deionized water | Balance |

Example 16

Conditioning Shampoo

| | (wt. %) |
|---|---|
| Sulfate salt 1 (ammonium salt, a 25 wt. % aqueous solution) obtained in Preparation Example 1 | 64.0 |
| 2-Ethylhexyl glyceryl ether | 0.3 |
| Cocoyl monoethanolamide | 0.5 |
| Myristyl alcohol | 1.0 |
| Cetanol | 0.5 |
| Ethylene glycol distearate | 3.0 |
| Cationic hydroxyethyl cellulose *7 | 0.2 |
| Cationic guar gum *12 | 0.3 |
| Glycerin | 1.0 |
| Amino-modified silicone derivative *3 | 1.5 |
| Highly polymerized methylpolysiloxane emulsion ("Silicone CF2450", trade name; product or Dow Corning Toray) | 1.0 |
| Sodium chloride | 0.2 |
| Benzyloxyethanol | 0.5 |
| Malic acid | 0.7 |
| Lactic acid | Amount to adjust pH to 3.7 |
| Deionized water | Balance |

*12 "Jaguar C-13S", trade name; product of Rhodia (molecular weight: 300000, cationic charge density: 1.4 meq/g)

Example 17

Conditioning Shampoo

| | (wt. %) |
|---|---|
| Sulfate salt 2 (ammonium salt, a 25 wt. % aqueous solution) obtained in Preparation Example 2 | 40.0 |
| Lauryl amidopropylbetaine | 3.0 |
| Polyoxyethylene (16) lauryl ether | 2.0 |
| Stearoxypropyldimethylamine•malate | 0.5 |
| Ethylene glycol distearate | 2.0 |
| Cationic guar gum *12 | 0.3 |
| Polypropylene glycol (Mw = 400) | 0.5 |
| Amino-modified silicone derivative *3 | 0.8 |
| Highly polymerized methylpolysiloxane emulsion ("Silicone CF2450", trade name; product or Dow Corning Toray) | 4.0 |
| Sodium chloride | 1.0 |
| Malic acid | 0.8 |
| Glycolic acid | 0.75 |
| Sodium chloride | Amount to adjust pH to 3.5 |
| Deionized water | Balance |

Example 18

Pearlescent Anti-Dandruff Shampoo

| | (wt. %) |
|---|---|
| Sulfate salt 1 (ammonium salt, a 25 wt. % aqueous solution) obtained in Preparation Example 1 | 52.0 |
| Isodecyl glyceryl ether | 1.5 |
| Cocoyl amidopropylbetaine | 1.0 |
| Lauryl hydroxysulfobetaine | 1.0 |
| Lauric acid | 0.5 |
| Oleic acid | 0.7 |
| Distearyl ether | 2.0 |
| Cocoyl benzalkonium chloride | 0.5 |
| Cationic hydroxyethyl cellulose *11 | 0.4 |
| Ethanol | 0.5 |
| Amino-modified silicone derivative *3 | 0.2 |
| Highly polymerized methylpolysiloxane emulsion ("Silicone CF2450", trade name; product or Dow Corning Toray) | 2.0 |
| Fucus vesiculosus extract | 0.05 |
| Malic acid | 0.7 |
| Sodium hydroxide | Amount to adjust pH to 5.5 |
| Deionized water | Balance |

Example 19

Pearlescent Shampoo

| | (wt. %) |
|---|---|
| Sulfate 3 (sodium salt, a 25 wt. % aqueous solution) obtained in Preparation Example 3 | 48.0 |
| Sodium cocoamphoacetate | 0.5 |
| Cocoyl monoethanolamide | 0.3 |
| Polyoxyethylene (14) lauryl ether | 1.0 |
| Ethylene glycol distearate | 2.0 |
| Cationic hydroxyethyl cellulose *11 | 0.4 |

-continued

| | (wt. %) |
|---|---|
| Highly polymerized methylpolysiloxane emulsion *5 | 1.5 |
| Panthenol | 0.05 |
| Silk extract | 0.05 |
| Sodium chloride | 1.0 |
| Lactic acid | Amount to adjust pH to 6.0 |
| Deionized water | Balance |

Example 20

Conditioning Shampoo

| | (wt. %) |
|---|---|
| Sulfate salt 1 (ammonium salt, a 25 wt. % aqueous solution) obtained in Preparation Example 1 | 52.0 |
| Isodecyl glyceryl ether | 0.7 |
| Lauryl amidopropylbetaine | 2.0 |
| Cocoyl monoethanolamide | 0.5 |
| Myristyl alcohol | 1.5 |
| Polyoxyethylene (16) lauryl ether | 1.0 |
| Ethylene glycol distearate | 2.0 |
| Cationic hydroxyethyl cellulose *6 | 0.5 |
| Diallyl quaternary ammonium salt/acrylamide copolymer *8 | 0.2 |
| Amino-modified silicone ("SM 8704C", trade name; product of Dow Corning Toray) | 0.8 |
| Highly polymerized methylpolysiloxane emulsion *5 | 2.0 |
| Benzyl alcohol | 0.4 |
| Polypropylene glycol (Mw = 400) | 0.2 |
| Sodium chloride | 1.0 |
| Hydrolyzed conchiolin solution (dry content: 3 wt. %) | 0.05 |
| Asian ginseng extract (dry content: 3 wt. %) | 0.05 |
| Soybean extract (dry content: 0.4 wt. %) | 0.05 |
| Eucalyptus extract (dry content: 0.2 wt. %) | 0.05 |
| Rice bran oil | 0.05 |
| Malic acid | 0.5 |
| Sodium hydroxide | Amount to adjust pH to 3.9 |
| Deionized water | Balance |

Example 21

Conditioning Shampoo

| | (wt. %) |
|---|---|
| Sulfate salt 1 (ammonium salt, a 25 wt. % aqueous solution) obtained in Preparation Example 1 | 48.0 |
| 2-Ethylhexyl glyceryl ether | 0.3 |
| Cocoyl monoethanolamide | 0.5 |
| Myristyl alcohol | 1.0 |
| Cetanol | 0.5 |
| Ethylene glycol distearate | 3.0 |
| Cationic hydroxyethyl cellulose *7 | 0.2 |
| Cationic guar gum *12 | 0.3 |
| Glycerin | 1.0 |
| Highly polymerized methylpolysiloxane emulsion *5 | 1.0 |
| Sodium chloride | 0.2 |
| Benzyloxyethanol | 0.5 |
| Malic acid | 0.7 |
| Lactic acid | Amount to adjust pH to 3.7 |
| Deionized water | Balance |

Example 22

Conditioning Shampoo

| | (wt. %) |
|---|---|
| Sulfate salt 2 (ammonium salt, a 25 wt. % aqueous solution) obtained in Preparation Example 2 | 40.0 |
| Lauryl amidopropylbetaine | 3.0 |
| Polyoxyethylene (16) lauryl ether | 2.0 |
| Stearoxypropyldimethylamine•malate | 0.5 |
| Ethylene glycol distearate | 2.0 |
| Cationic guar gum *12 | 0.3 |
| Polypropylene glycol (Mw = 400) | 0.5 |
| Highly polymerized methylpolysiloxane emulsion *5 | 1.0 |
| Sodium chloride | 1.0 |
| Malic acid | 0.8 |
| Glycolic acid | 0.75 |
| Sodium chloride | Amount to adjust pH to 3.5 |
| Deionized water | Balance |

Example 23

Pearlescent Anti-Dandruff Shampoo

| | (wt. %) |
|---|---|
| Sulfate salt 1 (ammonium salt, a 25 wt. % aqueous solution) obtained in Preparation Example 1 | 52.0 |
| Isodecyl glyceryl ether | 1.5 |
| Cocoyl amidopropylbetaine | 1.0 |
| Lauryl hydroxysulfobetaine | 1.0 |
| Lauric acid | 0.5 |
| Oleic acid | 0.7 |
| Distearyl ether | 2.0 |
| Cocoyl benzalkonium chloride | 0.5 |
| Cationic hydroxyethyl cellulose *11 | 0.4 |
| Ethanol | 0.5 |
| Highly polymerized methylpolysiloxane emulsion *5 | 2.0 |
| Fucus vesiculosus extract | 0.05 |
| Malic acid | 0.7 |
| Sodium hydroxide | Amount to adjust pH to 5.5 |
| Deionized water | Balance |

The shampoos obtained in Examples 7 to 23 each featured speedy foaming and smoothness of foam during shampooing, smoothness of the hair during rinsing, and excellent luster and manageability of the hair after shampooing.

The invention claimed is:

1. An aqueous hair cleansing composition comprising the following components (A), (B) and (C):

(A) from 5 to 30 wt. % of a sulfate surfactant having sulfates which are represented by the following formula (1):

$$R-O-(C_2H_4O)_n-SO_3M \quad (1),$$

wherein, R represents a linear or branched $C_{8-18}$ alkyl or alkenyl group, n is 0 or a positive integer and M represents sodium or ammonium, and are composed of from 30 to 45 wt. % of a sulfate of the formula (1) in which n=0, from 18 to 27 wt. % of a sulfate of the formula (1) in which n=1, from 10 to 20 wt. % of a sulfate of the formula (1) in which n=2, and the balance of sulfates of the formula (1) in which n=3 or greater, and containing the sulfates of the formula (1) in which n=0 to 2 in a total amount of 70 wt. % or greater based on all the sulfates;

(B) from 0.05 to 10 wt. % of an amino-modified silicone derivative represented by the following formula (3):

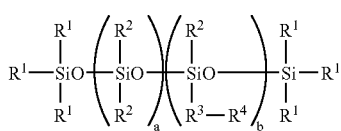 (3)

wherein, each $R^1$ independently represents a monovalent hydrocarbon group, hydroxy group or alkoxy group, each $R^2$ independently represents a monovalent hydrocarbon group, each $R^3$ independently represents a divalent $C_{1-10}$ hydrocarbon group, each $R^4$ independently represents a group represented by the following formula (4) or (5):

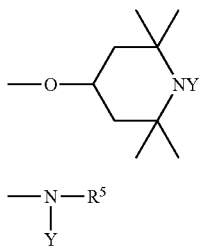

(4)

—N—R$^5$
  |
  Y (5)

in which, each Y independently represents a hydrogen atom or a group —CH$_2$—CH(OH)—R$^3$—OH, each R$^5$ independently represents a hydrogen atom or a group —R$^3$NY$_2$, wherein Y and R$^3$ have the same meanings as defined above, with the proviso that the all of the Y do not represent a hydrogen atom simultaneously, a is from 25 to 1000 and b is from 1 to 200; and (C) from 0.1 to 10 wt. % of a silicone oil represented by the following formula (2):

R'(CH$_3$)$_2$SiO—[(CH$_3$)$_2$SiO]$_m$—Si(CH$_3$)$_2$R'     (2), wherein, R' represents a methyl or hydroxy group and m is from 50 to 20000, and existing as disperse particles having an average particle size of less than 50 µm.

2. The aqueous hair cleansing composition according to claim 1, further comprising one or more surfactants selected from the group consisting of a nonionic surfactant and an amphoteric surfactant.

3. The aqueous hair cleansing composition according to claim 1, further comprising a cationic polymer.

4. The aqueous hair cleansing composition according to claim 1, further comprising a silicone other than Components (B) and (C).

5. The aqueous hair cleansing composition according to claim 1, further comprising a pearling agent wherein the pearling agent comprises at least one selected from the group consisting of an ethylene glycol monoalkyl ester and an ethylene glycol dialkyl ester.

6. The aqueous hair cleansing composition according to claim 1, further comprising a higher alcohol.

7. The aqueous hair cleansing composition according to claim 3, wherein the cationic polymer is at least one selected from the group consisting of an alkyltrimethylammonium salt, an alkoxytrimethylammonium salt, a dialkyldimethylammonium salt, an alkyldimethylamine, an alkyldimethylamine salt, an alkoxydimethylamine, an alkoxydimethylamine salt, an alkylamidodimethylamine and an alkylamidodimethylamine salt.

8. The aqueous hair cleansing composition according to claim 4, wherein the silicone other than Components (B) and (C) is at least one selected from the group consisting of a dimethylpolysiloxane, an amino-modified silicone, a polyether modified silicone, a methylphenylpolysiloxane, a fatty acid modified silicone, an alcohol modified silicone, an alkoxy modified silicone, an epoxy modified silicone, a fluorine modified silicone, a cyclic silicone and an alkyl modified silicone.

9. The aqueous hair cleansing composition according to claim 6, wherein the higher alcohol is at least one selected from the group consisting of myristyl alcohol, cetyl alcohol, oleyl alcohol, stearyl alcohol, isostearyl alcohol, behenyl alcohol, 2-octyldodecanol and cetostearyl alcohol.

* * * * *